United States Patent [19]

Sanderson et al.

[11] Patent Number: 4,517,374

[45] Date of Patent: May 14, 1985

[54] CYCLOALKANE EPOXIDES PRODUCED BY AIR OXIDATION OF CYCLOALKENES OVER OXIDE CATALYSTS

[75] Inventors: John R. Sanderson; Lewis W. Watts, Jr.; Terry L. Renken, all of Austin, Tex.

[73] Assignee: Texaco Inc., White Plains, N.Y.

[21] Appl. No.: 510,142

[22] Filed: Jul. 1, 1983

[51] Int. Cl.$^3$ ............................................ C07D 301/06
[52] U.S. Cl. ..................................... 549/533; 560/246
[58] Field of Search ................ 549/533, 1, 9; 560/246

[56] References Cited

U.S. PATENT DOCUMENTS

| | | | |
|---|---|---|---|
| 3,333,010 | 7/1967 | Urbanek | 549/533 |
| 4,069,381 | 1/1978 | Gaenzler et al. | 560/1 |
| 4,220,800 | 9/1980 | Stapp | 560/1 |

*Primary Examiner*—Norma S. Milestone
*Attorney, Agent, or Firm*—Robert A. Kulason; Jack H. Park; David L. Mossman

[57] ABSTRACT

A process for the production of cycloalkane epoxides from cycloalkenes in the presence of an oxide catalyst, oxygen and a carboxylate ion source via air oxidation is described. The oxide catalyst may have as a cation boron, chromium, iron, nickel, copper, zinc or terbium or mixtures thereof. Combination catalysts such as ferric oxide/zinc oxide and nickel oxide/copper oxide/chromium oxide/boric oxide complexes are also found to be useful. The reaction is conducted at a temperature in the range of 50° to 150° C. and a pressure of one atmosphere or greater. Cycloalkane epoxides are useful in the preparation of resins, plasticizers, etc.

2 Claims, No Drawings

CYCLOALKANE EPOXIDES PRODUCED BY AIR OXIDATION OF CYCLOALKENES OVER OXIDE CATALYSTS

BACKGROUND OF THE INVENTION

1. Field of the Invention

The invention is related to a process for the production of cycloalkane epoxides by the air oxidation of cycloalkenes, and is particularly related to such a process conducted in the presence of an oxide catalyst.

2. Description of Relevant Methods

The production of ethylene oxide from ethylene has long been known. However, there has been a less successful search for a similar process for producing other oxides directly from olefins in an economic manner. The same processes which produced ethylene oxide cannot be adapted to the production of other oxides.

As a result, a number of different schemes to produce olefin oxides from olefins or to produce an intermediate to olefin oxides from olefins have been proposed. One segment of the research effort seemed to be directed to producing an olefin oxide directly from the olefin in the presence or absence of a solvent. U.S. Pat. No. 2,649,463 describes the production of a coordination complex created by the reaction of an olefin with a metal halide where the metal is copper, platinum, palladium, iridium, aluminum, zinc, silver, mercury or antimony. This coordination complex is further reacted with oxygen at a high temperature to produce the olefin oxide plus oxygen-containing metal halides. Hawkins, et al. in an article entitled, "Autoxidation of Olefins," in the *Journal of Applied Chemistry*, Vol. 6, 1956, pgs 1 through 10, describes a process for the production of epoxides directly from olefins and molecular oxygen over magnesium oxide and/or cobalt naphthenate. The direct production of olefin oxides from a mono olefin and a saturated hydrocarbon with oxygen and water, organic acids or olefin oxide in low concentration is described in U.S. Pat. No. 2,780,634.

Brill, et al. in *Journal of Organic Chemistry*, Vol. 29, 1964, pgs 140-143, describes a process for passing olefins and oxygen, frequently in contact with or dissolved in benzene over various catalysts such as azobisisobutyronitrile, cadmium oxide, cobaltic acetylacetonate, magnesium oxide or methyl ethyl ketone peroxide to produce various oxidation products, including the desired epoxides. U.S. Pat. No. 3,132,156 reveals that ethylene, propylene or butylene oxide may be produced directly from ethane, propane or butane under very precise conditions. These conditions include a temperature of between 425° to 575° C., an oxygen volume percent of between 4 and 14, a contact time with the oxygen of between 0.07–1.5 seconds, a pressure of between 20 to 150 psig and constant concentrations of reactants. Epoxides may also be produced from olefins and oxygen which are in an inert reaction medium when they are brought in contact with a rhenium catalyst and 0.05 to 15 weight percent of a reaction modifier comprised of an alkyl aryl or cyclo alkyl cyanide, pyridine or quinoline in accordance with the invention described in U.S. Pat. No. 3,316,279.

Other schemes for producing olefin oxides from olefins and oxygen by means of a solvent or liquid reaction medium include the following. U.S. Pat. No. 3,153,058 employs polyacyl esters of polyhydroxy alkanes, polyhydroxy cycloalkanes, polyglycols or mixtures thereof as the solvent. Materials selected from saturated aliphatic, alicyclic and aromatic nitriles and mixtures thereof form the solvent in U.S. Pat. No. 3,210,180. Boric acid esters form the liquid reaction medium in U.S. Pat. No. 3,210,381. U.S. Pat. No. 3,228,967 uses major amounts of acetone as the solvent. Carbonic acid esters are employed in U.S. Pat. No. 3,228,968, and at least 25 percent by weight of certain ketones serves as the reaction medium in U.S. Pat. No. 3,232,957. Halogenated benzenes serve as the solvent in U.S. Pat. No. 3,238,229 while benzoic acid esters are employed in a similar reaction described in U.S. Pat. No. 3,281,433. Olefin oxides may be prepared directly from olefins and oxygen over a hydrocarbon soluble, phosphorous molybdenum-hydroxy compound catalyst according to the disclosure in U.S. Pat. No. 3,856,826. The approach of making epoxides directly has never been commercially feasible because all of the methods explored gave low yields of epoxides.

Some of the more recent patents in this field include the following methods to make glycol esters which are precursors to the epoxides. Esters may be produced from olefins in an acid plus oxygen over a tin or cerium catalyst in the presence of iodide as revealed by U.S. Pat. No. 4,154,957. Saturated vicinal esters may be produced from olefins, carboxylic acids and oxygen in the presence of a boron-containing catalyst according to the invention of U.S. Pat. No. 4,220,800. U.S. Pat. No. 4,221,916 teaches that olefins, carboxylic acids and oxygen when reacted together over a vanadium or ruthenium-containing catalyst can also produce saturated vicinal esters. U.S. Pat. No. 4,238,624 discloses a procedure by which ethylene, oxygen and a lower alkanoic acid are reacted together over an iodine source in a bismuth stabilized tellurium oxide catalyst on a carbon support to give ethylene glycol mono- and dialkanoates. U.S. Pat. No. 4,069,381 reveals how glycol monoesters may be made from olefins, oxygen and carboxylic acids over a catalyst system where the cation is zirconium, niobium, molybdenum, hafnium, tantalum, tungsten or rhenium where the anion is a halide in the presence of lithium, sodium, potassium, titanium, vanadium, chromium, manganese, iron, cobalt, nickel, copper, zinc, aluminum or silver.

Methods also exist for converting the ester intermediates into the epoxides. For example, U.S. Pat. No. 4,012,423 describes how vicinal hydroxy esters may be reacted over group I, II and IIIA basic metal carboxylates, being the preferred catalyst (sodium, potassium, lithium, calcium or barium, etc.), or group I, II and IIIA basic metal simple oxides and complex oxides and organic bases (such as borates, phosphates, oxides and carboxylates, particularly sodium borate, nickel oxide, etc.) to give epoxides. Another method is described in U.S. Pat. No. 4,158,008 whereby propylene glycol monoesters in the presence of a high boiling solvent is reacted over a base to produce propylene oxide. Propylene oxide may also be produced from propylene glycol with the removal of a water molecule over a weakly acidic carrier comprising a basic alkali metal salt of a low molecular weight carboxylic acid as taught by U.S. Pat. No. 4,226,780.

Cycloalkenes are also known to be oxidized. Boron-containing catalysts, in the form of boric acid, boric oxide and boron trialkoxy compounds, are also used in the oxidation of 1,5,9-cyclododecatriene according to Japanese Pat. No. 73-21,936 (Chemical Abstracts 79:104812p). Cyclooctene was oxidized with air at 110°

C. for twelve hours in the presence of cobalt naphthenate to give 22% conversion, 56% selectivity to epoxide and 14% selectivity to alcohol plus ketone, according to German Offenlegungsschrift No. 923,185 (CA 52:4685).

European patent application No. 31,537 teaches epoxide production from olefins, including cycloalkenes, and hydrogen peroxide in an anhydrous solvent containing boron catalysts, such as orthoboric acid. The epoxidation of cyclododecene with performic acid formed in situ is described in European patent application No. 34,206. Methods for the direct oxidation of olefins, including cycloalkenes, in the liquid phase by reacting the olefin with hydrogen peroxide in the presence of a boron-containing catalyst; e.g., boron oxides, boron oxyacids, boron halides and the like, are described in U.S. Pat. Nos. 4,303,586 and 4,303,587. Finally, the liquid phase oxidation of high molecular weight alpha olefins gave poor yields to the epoxides according to C. J. Norton, et al. in *Oxidation of Organic Compounds*, Vol. I, Advances in Chemistry Series 75, American Chemical Society, Washington, 1968, p. 89, et seq.

U.S. Pat. No. 3,014,928 teaches that the monoepoxide of cyclododecatriene may be formed by the reaction of cyclododecatriene with various per compounds such as monoperacetate, performic acid, perbenzoic acid and peracetic acid in over 90% yields.

Despite all of the investigative routes described so far and the ones that have been devised which have not been described, there is still a need for an efficient method for making cycloalkylene oxides from cyclic olefins, which does not involve a highly corrosive or highly expensive catalyst system.

SUMMARY OF THE INVENTION

The invention concerns a process for the production of cycloalkane epoxides comprising reacting a cycloalkene with oxygen under epoxidation conditions in the presence of an oxide catalyst where the cation is selected from the group consisting of boron, chromium, iron, nickel, copper, zinc and terbium or mixtures thereof.

DETAILED DESCRIPTION OF THE PREFERRED EMBODIMENTS

Cycloalkane epoxides, also called cycloalkene oxides, may be prepared by the oxygen or air oxidation of olefins in a solvent which is a carboxylate ion source in the presence of at least one of a number of oxide catalysts. The epoxides are useful as intermediates for the preparation of resins, plasticizers and other useful products.

According to the method of this invention, the useful feedstocks are cycloalkenes, or cyclic olefins, having at least one double bond located anywhere within the molecule. It is anticipated that mixtures of olefins may also be used. Specific examples of suitable feedstocks include, but are not limited by, the following list: cyclohexene, cyclooctene, cyclodecene, cyclododecene, etc. and mixtures thereof. Preferably, the olefin has 5 to 16 carbon atoms. Cyclic olefins with two, three and more double bonds are also permitted.

When other alkenes (for example linear n-alkenes) are air oxidized in a carboxylic acid solvent, the main products are the various corresponding glycol esters. In contrast to the prior art, it is possible using conditions given in this invention (with certain cycloalkenes) to obtain the epoxide as the main product.

Of course, molecular oxygen in a pure form or in air is an essential co-reactant for the method of this invention.

The material which may be used as a solvent should be capable of generating a carboxylate ion when it serves as a solvent. These compounds may be generally described as carboxylic acids and anhydrides. They may include materials such as acetic acid, acetic anhydride, various carboxylic acids, etc., although acetic acid and acetic anhydride are the preferred solvents. Acetic anhydride and acetic acid may be used either separately or together. Some oxide catalysts can be expected to work well with one and not the other.

Oxide compounds are believed to be novel as catalysts of the reaction of cyclic olefins and oxygen to cyclic epoxides, never having been previously discovered. The preferred cations for use in these oxide catalysts include iron (in either valence II or III form), boron, chromium, nickel, copper, zinc, terbium or mixtures of these. Especially preferred as catalysts are ferric oxide, zinc oxide, iron (II, III) oxide or $Fe_3O_4$ are terbium oxide along with the combination complexes of ferric oxide/zinc oxide and nickel oxide/copper oxide/chromium oxide/boric oxide. The complex of oxides of nickel, copper and chromium is also useful for this reaction. This latter complex is known as a hydrogenation-dehydrogenation catalyst as revealed in U.S. Pat. No. 3,152,998, incorporated by reference herein, which also describes its preparation in detail. The other catalysts described herein are available commercially. The preferred catalyst levels for this reaction range from 0.0001 to 1.0 wt.%.

All of the catalysts of this invention give good results, which may be defined as a vapor phase chromatography area percent yield of 50% or more. The catalysts of this invention are much less corrosive than many of those used in other methods, especially the halide systems. Also, much smaller catalyst levels may be used. They are also less expensive than many of the catalyst systems proposed.

The reaction conditions under which the method of this invention may be conducted include a temperature range of from about 50° to 250° C. A preferred range is from 50° to 150° C. The pressure may be one atmosphere or higher. These reaction conditions are much milder than many of those in the prior art discussed earlier. The reaction may be performed in a batch or a continuous mode.

Common by-products of the instant reaction include the cycloalkane 1,2-diol (diacetate) or the cycloalkane hydroxyacetate. The hydroxyacetate may be pyrolyzed to the epoxide in the presence of a basic material such as sodium acetate at 250°–600° C. according to British Pat. No. 1,446,395. The diacetate may be converted to the epoxide by a similar route if the diacetate is first hydrolyzed to the hydroxyacetate. Therefore, the diacetate and the hydroxyacetate by-products are also valuable and may be considered as intermediates to the epoxides.

The invention may be further illustrated by the following examples which are not intended to limit the scope of the invention.

EXAMPLE I

Cyclooctene Oxidation Over Zinc Oxide/Iron Oxide Catalyst

A small resin flask was fitted with a condenser, mechanical stirrer, fritted glass addition tube and thermometer. Acetic acid (70 ml), cyclooctene (from Aldrich Chemical, 95% pure, 20 ml) and $ZnO \cdot Fe_2O_3$ (0.20 g) were charged to the flask. The mixture was heated to 100° C. and air bubbled through the reaction mixture for 21.5 hours at 40–50 ml/minute. The temperature was maintained at 100° C.±2° C. by means of a Therm-O-Watch temperature regulator. At the end of the reaction, the mixture was poured into water and the aqueous layer drawn off and discarded. The organic layer was washed three times with water and dried over anhydrous sodium sulfate. Infrared analysis showed a carbonyl band at about 5.8 microns and a small hydroxyl band at about 2.9 microns. Nuclear magnetic resonance analysis showed that the reaction mixture was 37 mole % cyclooctene and 52 mole % epoxide (83% selectivity). In addition, there was 5–10% ester(s) present—most likely the hydroxy ester.

EXAMPLE II

Comparative Example Using Nickel Borate

Using a procedure essentially the same as in Example I except that 0.04 g of nickel borate was used as catalyst, cyclooctene was oxidized for 13.5 hours. After work up, infrared analysis indicated only a trace of ester. Nuclear magnetic resonance analysis indicated that the reaction mixture was essentially pure starting material.

EXAMPLE III

Preparation of Nickel Oxide/Copper Oxide/Chromium Oxide Catalyst

A solution of $Ni(NO_3)_2 \cdot 5H_2O$ (726 g, 2.50 mole), $Cu(NO_3)_2 \cdot 6H_2O$ (214 g, 0.723 mole), $Cr(NO_3) \cdot 9H_2O$ (112 g, 0.280 mol) in 1600 ml of deionized water and a solution of $Na_2CO_3$ (433 g, 4.08 mole) in 1900 ml of deionized water were added simultaneously to 1,000 ml of rapidly stirred deionized water at 80° C. The additions took place over 1.5 hour. The rates of addition were adjusted so the solution pH remained close to 7.0. After two hours of stirring at 80° C., the precipitated carbonates were removed by filtration. The filter cake was washed by adding to it 2,000 ml of fresh deionized water, heating the resultant slurry to 80° C. with rapid stirring, followed by filtration. The washing and filtration steps were repeated six additional times. The filter cake was dried at 140° C. in air and then calcined overnight at 400° C. The powdered metal oxides were reduced at 280°–300° C. in an $H_2/N_2$ gas stream, followed by partial oxidation at 25°–65° C. with a stream of air/$N_2$ to stabilize the catalyst to atmospheric conditions. The resultant powder contained 54.4 wt.% Ni, 22.9 wt.% Cu and 5.2 wt.% Cr.

EXAMPLE IV

Preparation of Iron Oxide/Nickel Oxide/Copper Oxide/Chromium Oxide Catalyst

This catalyst was prepared using essentially the same procedure as that described for the Ni-Cu-Cr catalyst of Example III. The solution of metal nitrates contained 9.9 mole % $Fe(NO_3) \cdot 9H_2O$ in addition to the other metal nitrates which were in the catalyst of Example III.

EXAMPLE V

Preparation of Catalyst Containing Oxides of Nickel, Copper, Chromium and Boron This catalyst was prepared using essentially the same procedure as that described for the Ni-Cu-Cr catalyst of Example III except that a mixture of the metal carbonates and borates were precipitated. A 3:1 molar ratio of $Na_2CO_3$ to $Na_2B_4O_7 \cdot 10H_2O$ was used in the precipitation of the metal salts. The resultant catalyst contained 50.1 wt.% Ni, 19.8 wt.% Cu, 3.88 wt.% Cr and 6.67 wt.% B.

EXAMPLES VI–XV

The remaining examples use a variety of catalysts. Two comparative examples are included. Example VI uses no catalyst while Example VII employs boric anhydride as the catalyst as taught by U.S. Pat. No. 4,220,800, previously discussed.

All examples follow the procedure described below and the results are tabulated in Table I.

A small resin flask was fitted with a condenser, a mechanical stirrer, a fritted glass addition tube and a thermometer. Acetic acid (70–100 ml), cyclododecene (20–30 ml) and a catalyst (0.10–0.20 g) were charged to the flask and the mixture heated to 100° C. Air was bubbled through the reaction mixture at 40–50 ml/minute for 15 to 20 hours. The temperature was maintained at 100±2° C. by means of a Therm-O-Watch temperature regulator. At the end of the reaction, the mixture was poured into water and the aqueous layer drawn off and discarded. The upper layer was washed three times with water, dried over anhydrous sodium sulfate and analyzed by vapor phase chromatography (VPC). The results in terms of area percent from vapor phase chromatography should be used only to compare one example to another. They are not meant to be an absolute measure in terms of, for example, the weight percent of a component in a product stream.

Combination oxide catalysts were also found to be useful, as seen in Examples IX and XI.

TABLE I

Oxidation of Cyclic Olefins Using Various Oxide Catalysts

| Ex. | Catalyst | Conversion, % | Selectivity, % | | Yield, % |
|---|---|---|---|---|---|
| | | | Epoxide | Esters | Total | |
| VI | None | 61.6 | 64.4 | 11.2 | 75.6 | 46.6 |
| VII | Boric Anhydride | 52.5 | 70.1 | 10.1 | 80.2 | 42.1 |
| VIII | Ni/Cu/Cr Catalyst from Ex. III | 40.7 | 53.6 | 14.0 | 67.6 | 27.5 |
| IX | Ni/Cu/Cr/B Catalyst from Ex. V | 62.9 | 64.1 | 15.9 | 80.0 | 50.3 |
| X | Fe/Ni/Cu/Cr Catalyst from Ex. IV | 65.3 | 14.4 | 6.6 | 21.0 | 13.7 |
| XI | Ferric-Zinc Oxide Complex Salt | 84.1 | 64.6 | 15.7 | 80.3 | 67.5 |
| XII | Ferric Oxide | 84.4 | 59.6 | 18.5 | 78.1 | 65.9 |
| XIII | Zinc Oxide | 72.9 | 65.6 | 15.4 | 81.0 | 59.0 |
| XIV | $Fe_3O_4$ Iron (II,III) Oxide | 88.9 | 65.1 | 18.8 | 83.9 | 74.6 |
| XV | Terbium Oxide | 71.2 | 67.8 | 13.8 | 81.6 | 58.1 |

Many modifications may be made in the method of this invention by those skilled in the art to maximize the yields of the desired epoxides (or acetates, as the case may be) without departing from the spirit and scope of the invention which is defined only by the appended claims. For example, one skilled in the art could determine an exact combination of catalysts, temperatures, feedstocks and modes of addition to optimize the yield of the desired product.

We claim:

1. A method for the production of cyclododecane epoxide comprising reacting cyclododecene with oxygen in the presence of zinc oxide as catalyst where acetic acid is also present under a temperature in the range of about 50° to 150° C.

2. The method of claim 1 in which the catalyst level is in the range from 0.0001 to 1.0 wt.%.

* * * * *